(12) United States Patent
Buczynski et al.

(10) Patent No.: US 8,132,870 B2
(45) Date of Patent: Mar. 13, 2012

(54) SHELF ASSEMBLY

(75) Inventors: Peter J. Buczynski, Girard, PA (US); James M. Szumigala, Erie, PA (US); Joseph B. Ott, Erie, PA (US); Michael A. Bacik, Fairview, PA (US); Michael A. Centanni, Parma, OH (US)

(73) Assignee: STERIS Inc., Temecula, CA (US)

( * ) Notice: Subject to any disclaimer, the term of this patent is extended or adjusted under 35 U.S.C. 154(b) by 938 days.

(21) Appl. No.: 12/033,903

(22) Filed: Feb. 20, 2008

(65) Prior Publication Data
US 2008/0218047 A1 Sep. 11, 2008

Related U.S. Application Data

(60) Provisional application No. 60/893,134, filed on Mar. 6, 2007, provisional application No. 60/962,876, filed on Aug. 1, 2007.

(51) Int. Cl.
*A47B 81/00* (2006.01)

(52) U.S. Cl. .............. 312/286; 312/334.12; 312/334.44; 108/143

(58) Field of Classification Search .................. 108/102, 108/137, 143; 312/333, 334.7, 334.8, 334.12, 312/334.16, 334.18, 334.44, 286, 301; 134/135; 422/24, 28, 298, 305
See application file for complete search history.

(56) References Cited

U.S. PATENT DOCUMENTS

| | | | | |
|---|---|---|---|---|
| 526,014 A * | 9/1894 | Hunter | ........................... | 220/550 |
| 2,212,330 A | 8/1940 | Thomas | ........................... | 250/52 |
| 2,565,784 A * | 8/1951 | Sheean | ........................... | 312/286 |
| 2,704,699 A * | 3/1955 | Evans | ........................... | 312/334.7 |
| 2,734,826 A | 2/1956 | Stentz | ........................... | 99/212 |
| 3,232,687 A * | 2/1966 | Mulreed | ........................... | 312/334.8 |
| 3,713,716 A * | 1/1973 | Stenger | ........................... | 312/107 |
| 3,860,309 A | 1/1975 | Brendgord | ........................... | 312/351 |
| 3,905,662 A | 9/1975 | Richmond | ........................... | 312/250 |
| 4,140,356 A | 2/1979 | Chervanak | ........................... | 312/350 |
| 4,170,421 A | 10/1979 | Balding et al. | ........................... | 366/144 |
| 4,183,596 A | 1/1980 | Greene et al. | ........................... | 312/333 |
| 4,440,461 A * | 4/1984 | Powell et al. | ........................... | 312/334.8 |
| 4,783,971 A * | 11/1988 | Alba | ........................... | 62/291 |
| 4,909,558 A * | 3/1990 | Roshinsky | ........................... | 296/37.6 |
| 4,935,604 A | 6/1990 | Allen et al. | ........................... | 219/400 |
| 5,389,336 A | 2/1995 | Childers | ........................... | 422/28 |
| 5,484,198 A * | 1/1996 | Pilliod | ........................... | 312/334.18 |
| 5,513,538 A | 5/1996 | Baker et al. | ........................... | 73/865.6 |

(Continued)

FOREIGN PATENT DOCUMENTS
DE 41 06 809 A1 4/1991
(Continued)

OTHER PUBLICATIONS

International Preliminary Report on Patentability, Application No. PCT/US2008/054341, dated Sep. 17, 2009.

(Continued)

*Primary Examiner* — James O Hansen
*Assistant Examiner* — Matthew Ing
(74) *Attorney, Agent, or Firm* — Renner, Otto, Boisselle & Sklar, LLP

(57) ABSTRACT

The disclosed invention relates to a bidirectional shelf assembly which may be used in a single door or double door cabinet. The cabinet may comprise the decontamination chamber of a decontamination unit. The cabinet may comprise a sterilizer and/or washer.

12 Claims, 4 Drawing Sheets

U.S. PATENT DOCUMENTS

| | | | |
|---|---|---|---|
| 5,590,940 A * | 1/1997 | Richard | 312/287 |
| 5,611,553 A * | 3/1997 | Schoeman et al. | 280/47.35 |
| 5,906,801 A | 5/1999 | Goughnour | 422/300 |
| 5,941,672 A | 8/1999 | Lapointe et al. | 414/401 |
| 6,074,000 A * | 6/2000 | Wagner | 297/188.11 |
| 6,250,730 B1 * | 6/2001 | Roth et al. | 312/333 |
| 6,666,218 B2 | 12/2003 | Lavoie et al. | 134/25.2 |
| 6,938,617 B2 * | 9/2005 | Le et al. | 126/339 |
| 2004/0001785 A1 | 1/2004 | Sullivan | 422/300 |
| 2005/0063884 A1 | 3/2005 | Sullivan et al. | 422/300 |
| 2005/0263015 A1 * | 12/2005 | Mulgrew | 99/516 |
| 2007/0035221 A1 * | 2/2007 | Koo | 312/404 |

FOREIGN PATENT DOCUMENTS

| | | |
|---|---|---|
| FR | 2 698 251 | 5/1994 |

OTHER PUBLICATIONS

International Search Report and Written Opinion, Application No. PCT/US2008/054341, mailed Oct. 6, 2008.

* cited by examiner

SHELF ASSEMBLY

This application claims benefit under 35 U.S.C. §119(e) to U.S. Provisional Application Ser. No. 60/893,134, filed Mar. 6, 2007, and U.S. Provisional Application Ser. No. 60/962,876, filed Aug. 1, 2007. These applications are incorporated herein by reference in their entireties.

TECHNICAL FIELD

This invention relates to shelf assemblies and, more particularly, to bidirectional shelf assemblies. These shelf assemblies may be used in single door or double door cabinets. These shelf assemblies may be used in sterilizers, washers and decontamination units. These shelf assemblies may be used in decontamination units employing double door decontamination chambers.

BACKGROUND

Decontamination units employing double door decontamination chambers typically use a loading cart or baskets to load contaminated articles into the decontamination unit and unload decontaminated articles from the decontamination unit. The contaminated articles are loaded at the front or "contaminated" side of the unit and the decontaminated articles are removed from the rear or "clean" side of the unit.

SUMMARY

A problem with the loading carts used in these decontamination units is that they need to be stored and can be a tripping hazard. A problem with baskets used in these units is that they typically require the use of loading and unloading platforms that take up space even when not in use. The present invention provides a solution to these problems. This invention relates to a bidirectional shelf assembly that may be used in a double door cabinet such as the decontamination chamber for a double door decontamination unit. The shelves of this assembly can extend outwardly from the decontamination unit on the front or contaminated side sufficiently to permit loading of contaminated articles, then slid into the decontamination unit to permit decontamination processing of the contaminated articles. Upon completion of the decontamination processing, the shelves can be extended outwardly from the decontamination unit at the rear or clean side sufficiently to permit unloading of the decontaminated articles. With this shelf assembly the requirement for loading carts, and loading and unloading platforms is eliminated. This shelf assembly may also be suitable for use in single door cabinets.

This invention relates to a shelf assembly, comprising: a shelf that is slideable in a first direction and a second direction, the shelf comprising a first end and second end; a first stationary support and a second stationary support, the first stationary support being positioned opposite the second stationary support, the first and second stationary supports slidably supporting the shelf, the first stationary support having a first end and a second end, the second stationary support having a first end and a second end; a first stationary stop mounted on the first stationary support near the first end of the first stationary support; a first traveling stop positioned near the second end of the shelf and adapted for contacting the first stationary stop when the shelf slides in the first direction; a second stationary stop mounted on the second stationary support at or near the second end of the second stationary support; and a second traveling stop positioned near the first end of the shelf and adapted for contacting the second stationary stop when the shelf slides in the second direction.

This invention also relates to a decontamination unit, comprising: a cabinet comprising one or more of the foregoing shelf assemblies, the cabinet including a first entrance with a first door and a second entrance with a second door, the first entrance being suitable for permitting one or more of the shelves to partially extend out of the cabinet through the first entrance when slid in the first direction, the second entrance being suitable for permitting one or more of the shelves to partially extend out of the cabinet through the second entrance when slid in the second direction; and a decontaminant generator for generating a decontaminant in the cabinet.

This invention also relates to a method of operating the foregoing decontamination unit, comprising: opening the first door; extending one or more of the shelves in the first direction partially through the first entrance; placing one or more contaminated articles on the one or more partially extended shelves; sliding the one or more partially extended shelves in the second direction into the cabinet; closing the first door; operating the decontaminant generator to generate a decontaminant in the cabinet for a sufficient period of time to decontaminate the one or more contaminated articles; opening the second door; extending the one or more shelves in the second direction partially through the second entrance; and removing the one or more decontaminated articles from the one or more partially extended shelves.

BRIEF DESCRIPTION OF THE DRAWINGS

In the annexed drawings all parts and features have like references. A number of the annexed drawings are schematic illustrations which are not necessarily proportioned accurately or drawn to scale.

DETAILED DESCRIPTION

All ranges and ratio limits disclosed in the specification and claims may be combined in any manner. It is to be understood that unless specifically stated otherwise, references to "a", "an", and/or "the" may include one or more than one, and that reference to an item in the singular may also include the item in the plural. All combinations specified in the claims may be combined in any manner.

The statement that the first stationary stop is mounted on the first stationary support "near the first end" of the first stationary stop refers to the first stationary stop being positioned closer to the first end of the first stationary support than the second end of the first stationary stop.

The statement that the second stationary stop is mounted on the second stationary support "near the second end" of the second stationary stop refers to the second stationary stop being positioned closer to the second end of the second stationary support than the first end of the second stationary stop.

The statement that the first traveling stop is positioned "near the second end" of the shelf refers to the first traveling stop being positioned closer to the second end of the shelf than the first end of the shelf.

The statement that the second traveling stop is positioned "near the first end" of the shelf refers to the second traveling stop being positioned closer to the first end of the shelf than the second end of the shelf.

Figure 1:
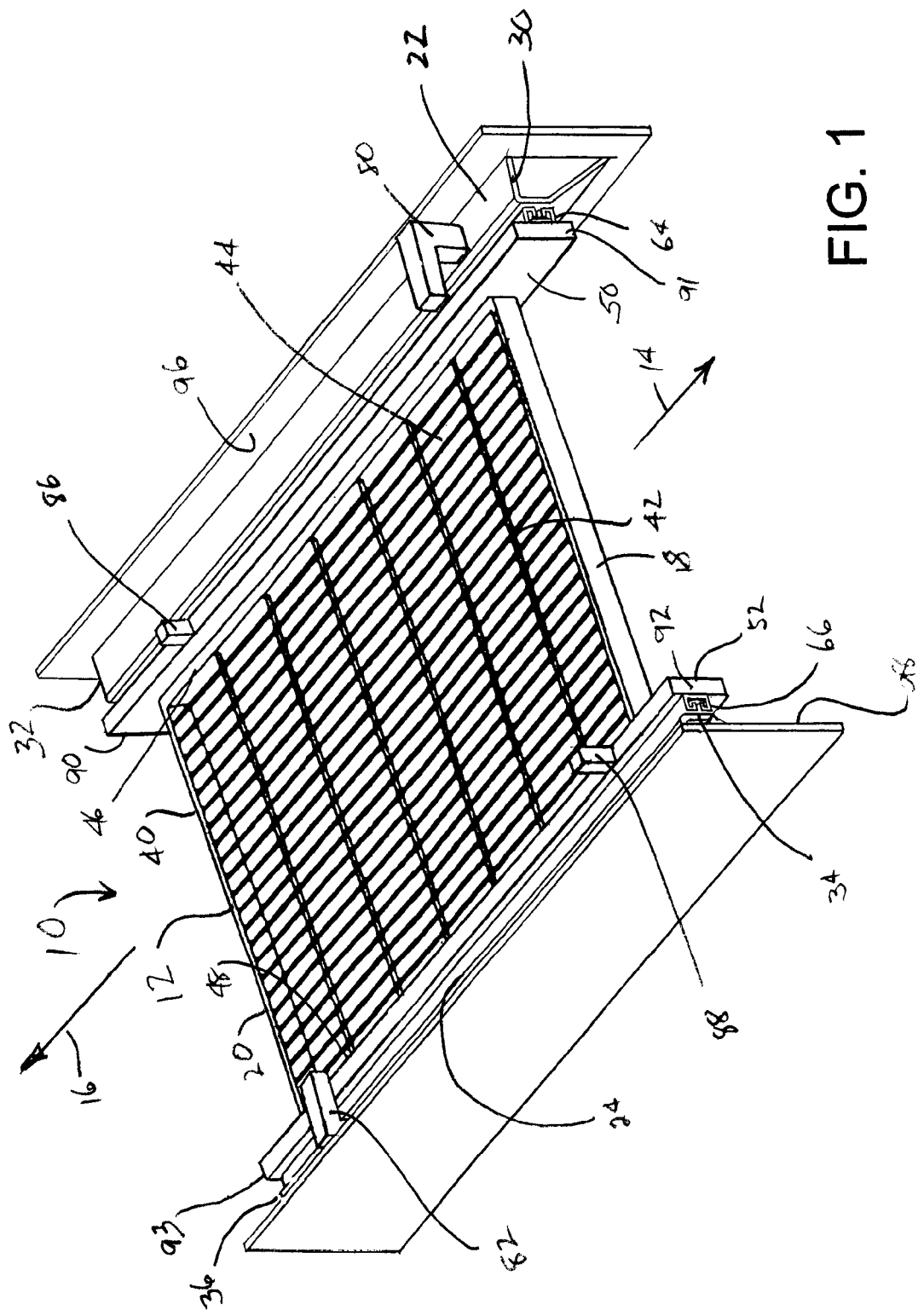
FIG. 1 is a schematic illustration of a shelf assembly within the scope of the present invention.
Figure 2:
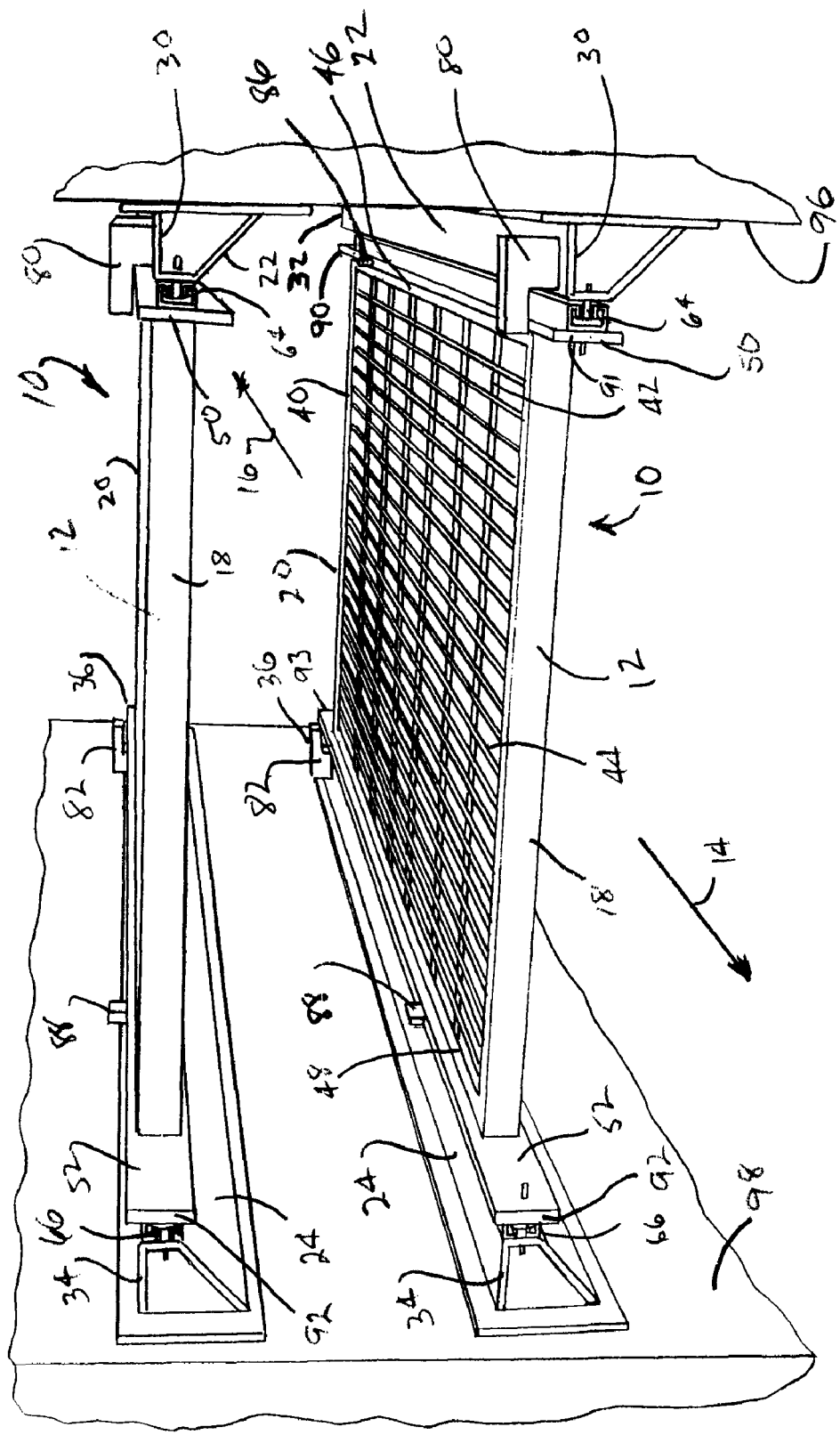
FIG. 2 is a schematic illustration of two of the shelf assemblies illustrated in FIG. 1 positioned one above the other.
Figure 3:
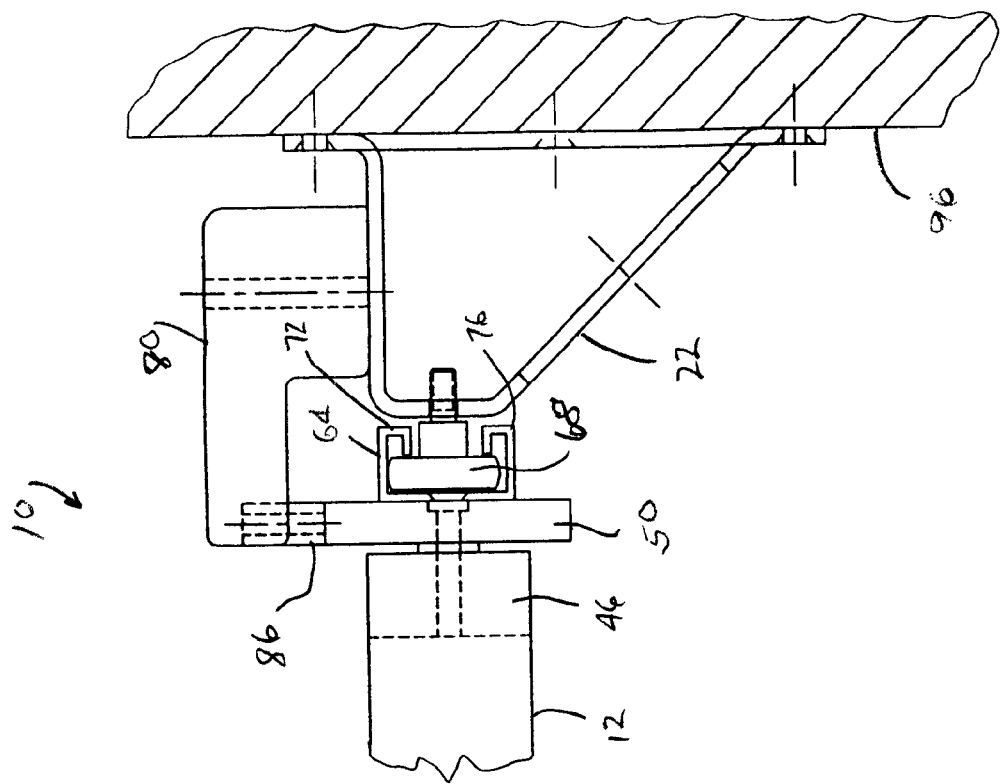
FIG. 3 is a schematic illustration of the shelf assembly illustrated in FIG. 1 with the shelf partially cut away, and the stationary and sliding stops shown in detail.
Figure 3:
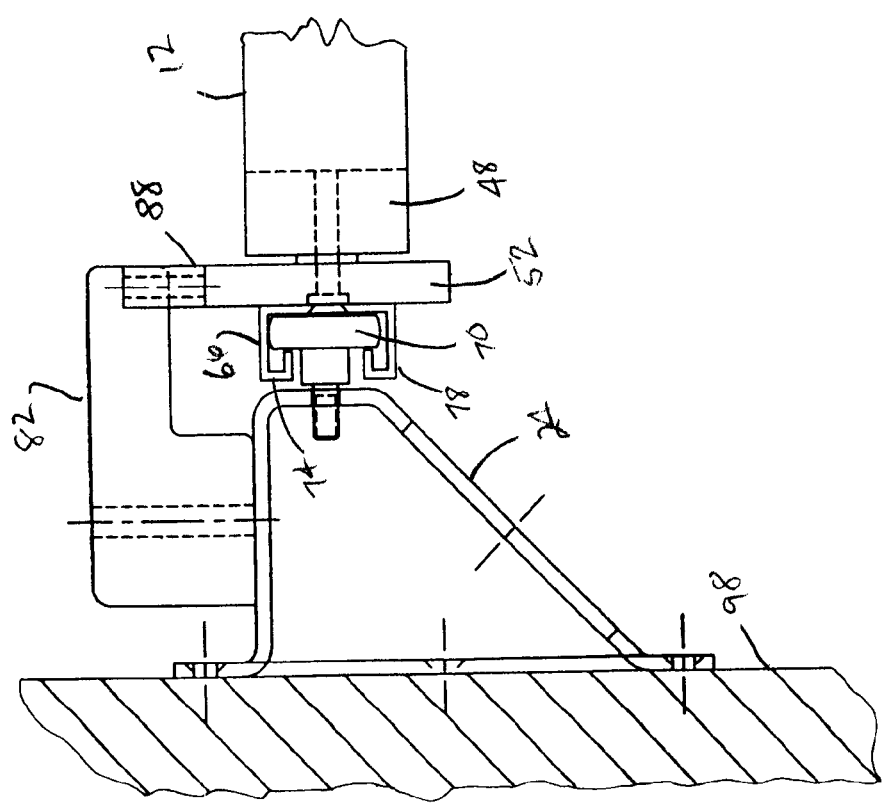

Referring to the drawings, and initially to FIGS. 1-3, the invention relates to shelf assembly 10, which comprises shelf 12. Shelf 12 is slideable in a first direction 14 and a second direction 16. The shelf 12 has a first end 18 and a second end 20. A first stationary support 22 is positioned on one side of the self 12 and a second stationary support 24 is positioned on the opposite side of the shelf 12. The shelf 12 is slidably supported by the first and second stationary supports 22 and 24. The first stationary support 22 has a first end 30 and a second end 32. The second stationary support 24 has a first end 34 and a second end 36.

The shelf 12 has a rectangular frame 40 with a grid of supports 42 running the width of the rectangular frame and supports 44 running the length of the rectangular frame. Alternatively, the shelf may comprise a flat or planar surface. The shelf 12 has a first longitudinal frame member 46 and a second longitudinal frame member 48. A first sliding support 50 is attached to the first longitudinal frame member 46. A second sliding support 52 is attached to the second longitudinal frame member 48. A first sliding shelf rail 64 is attached to the first sliding support 50. A second sliding shelf rail 66 is attached to the second sliding support 52. The first stationary support 22 has a plurality of first rollers 68, which are in the form of rotatable wheels, mounted on it. The first rollers 68 are adapted to be received by and fit in the first sliding shelf rail 64. The second stationary support 24 has a plurality of second rollers 70, which are in the form of rotatable wheels, mounted on it. The second rollers 70 are adapted to be received by and fit in the second sliding shelf rail 66. The first and second sliding shelf rails 64 and 66 are open channels. These channels have upper flanges 72 and 74, and lower flanges 76 and 78. The rollers 68 and 70 rotate within the channels but remain stationary while the sliding shelf rails 64 and 66 slide back and forth horizontally over the rollers in the directions 14 and 16. The flanges 72 and 74, and 76 and 78 prevent substantial vertical movement of the shelf 12. These flanges also permit stable horizontal movement of the shelf 12 without the shelf undergoing substantial tipping.

A first stationary stop 80 is mounted on the first stationary support 22 near the first end 30 of the first stationary support 22. The first stationary stop 80 comprises a projection extending vertically and horizontally from the first stationary support 22. A second stationary stop 82 is mounted on the second stationary support 24 near the second end 36 of the second stationary support 24. The second stationary stop 82 comprises a projection extending vertically and horizontally from the second stationary support 24. A first traveling stop 86 is mounted on the first sliding support 50 and comprises a projection extending vertically from the first sliding support 50. The first traveling stop 86 is positioned near the second end 90 of the first sliding support 50. The first traveling stop 86 is adapted for contacting the first stationary stop 80 when the shelf 12 slides in the first direction 14. A second traveling stop 88 is mounted on the second sliding support 52 and comprises a projection extending vertically from the second sliding support 52. The second traveling stop 88 is positioned near the first end 92 of the second sliding support 52. The second traveling stop 88 is adapted for contacting the second stationary stop 82 when the shelf 12 slides in the second direction 16.

Alternatively, the first stationary stop 80 may be mounted on the first sliding support 50 and the first traveling stop 86 may be mounted on the first stationary support 22. Similarly, the second stationary stop 82 may be mounted on the second sliding support 52 and the second traveling stop 88 may be mounted on the second stationary support 24. In effect, in this embodiment the stationary stops would be transformed to traveling stops, and the traveling stops would be transformed to stationary stops, but the overall operation would be the same. The first stationary stop 80 may comprise a projection extending vertically and horizontally from the first sliding support 50. The second stationary stop 82 may comprise a projection extending vertically and horizontally from the second sliding support 52. The first traveling stop 86 may comprise a projection extending vertically from the first stationary support 22. The first traveling stop 86 may be adapted for contacting the first stationary stop 80 when the shelf 12 slides in the first direction 14. The second traveling stop 88 may comprise a projection extending vertically from the second sliding support 52. The second traveling stop 88 may be adapted for contacting the second stationary stop 82 when the shelf 12 slides in the second direction 16.

The positioning of the stationary stops 80 and 82 and the traveling stops 86 and 88 may depend upon the number and strength of the rollers 68 and 70, as well as the design strength of shelf 12, sliding supports 50 and 52, sliding shelf rails 64 and 66 and stationary supports 22 and 24. The positioning of these stops may also depend on the amount of required movement for the shelf 12 in the directions 14 and 16, as well as the anticipated load to be carried by the shelf 12. These factors may be determined by the skilled artisan.

The positioning of stationary stops 80 and 82 relative to the ends of the stationary supports 22 and 24, and the positioning of the traveling stops 86 and 88 relative to the ends of the sliding supports 50 and 52 may be sufficient to permit a controlled horizontal sliding movement of the shelf 12 in the directions 14 and 16 to the extent desired and yet provide sufficient stability to avoid substantial tipping of the shelf 12. Substantial tipping may result in the articles placed on the shelf sliding off.

The positioning of the stationary stop 80 and the traveling stop 86 may be sufficient to permit a sliding movement of the shelf 12 in the direction 14 beyond the stationary stop 80 to the extent up to about 85% of the length of the shelf 12 as measured from first end 18 to second end 20, and in one embodiment up to about 75% of the length of the shelf 12, and in one embodiment up to about 50% of the length of the shelf 12, and in one embodiment up to about 35% of the length of the shelf 12 as measured from first end 18 to second end 20.

The positioning of the stationary stop 82 and the traveling stop 88 may be sufficient to permit a sliding movement of the shelf 12 in the direction 16 beyond the stationary stop 82 to the extent up to about 85% of the length of the shelf 12 as measured from second end 20 to first end 18, and in one embodiment up to about 75% of the length of the shelf 12, and in one embodiment up to about 50% of the length of the shelf 12, and in one embodiment up to about 35% of the length of the shelf 12 as measured from second end 20 to first end 18.

The permissible extent of the sliding movement of the shelf 12 in the direction 14 may be the same as or different than the permissible extent of the sliding movement of the shelf 12 in the direction 16.

Figure 4:
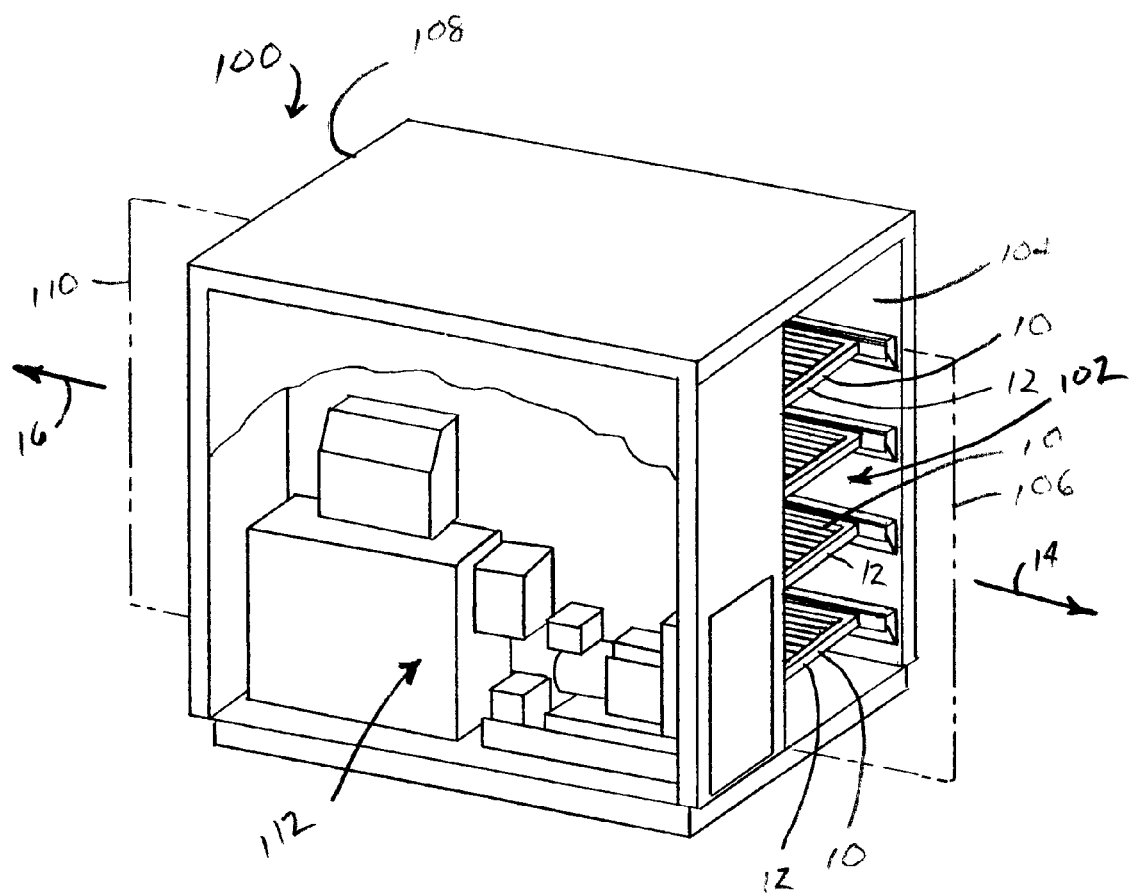
FIG. 4 is a schematic illustration of a decontamination unit containing a plurality of the shelf assemblies illustrated in FIG. 1, the shelf assemblies being positioned one above the other in the decontamination unit.

One or more of the shelf assemblies 10 may be positioned in a cabinet. The cabinet may be a single door cabinet or a double door cabinet. When the cabinet is a double door cabinet, it may have a first entrance and an opposite second entrance. The cabinet may comprise the decontamination chamber of a decontamination unit. The cabinet may comprise a sterilizer and/or a washer. When two or more of the shelf assemblies 10 are used, they may be positioned one above the other as illustrated in FIGS. 2 and 4. The first stationary support 22 may be mounted on a first interior wall 96 of the cabinet and the second stationary support 24 may be mounted on a second opposite interior wall 98 of the cabinet.

One or more of the shelf assemblies 10 may be used in a double door decontamination chamber of decontamination unit. Referring to FIG. 4, decontamination unit 100 comprises a double door decontamination chamber 102 which, as illustrated, has four of the shelf assemblies 10 positioned one above the other. It will be understood that any number of the shelf assemblies 10 may be used in the decontamination chamber 102, for example, from 1 to about 20 shelf assemblies, and in one embodiment from about 2 to about 10 shelf assemblies may be used. The decontamination chamber 102 includes a first entrance 104 with a first door 106, shown in phantom, and a second entrance 108 with a second door 110, shown in phantom. The first entrance 104 is suitable for permitting the shelf 12 to partially extend out of the decontamination chamber when slid in the first direction 14. The second entrance 108 is suitable for permitting the shelf 12 to partially extend out of the decontamination chamber when slid in the second direction 16. The decontamination unit 100 includes a decontaminant generator 112 for generating a decontaminant air stream comprising a decontaminant, such as vaporous hydrogen peroxide (VHP) or VHP in combination with ammonia, flowing the decontaminant air stream in the decontamination chamber 102 in contact with contaminated articles in the decontamination chamber 102 to decontaminate the contaminated articles, and removing gases from the decontamination chamber 102.

The decontamination unit 100 may be operated by opening the first door 106 and extending one or more of the shelves 12 in the first direction 14 partially through the first entrance 104; placing one or more contaminated articles on the one or more partially extended shelves 12; sliding the one or more shelves 12 in the second direction 16 into the decontamination chamber 102; closing the first door 104; operating the decontaminant generator 112 to generate a decontaminant air stream and flowing the decontaminant air stream in the decontamination chamber 102 for a sufficient period of time to decontaminate the one or more contaminated articles to produce one or more decontaminated articles; opening the second door 110; extending the one or more shelves 12 in the second direction 16 partially through the second entrance 108; and removing the one or more decontaminated articles from the one or more partially extended shelves 12.

The contaminated articles may be contaminated with any contaminant. The articles may comprise any article that may be placed on one or more of the shelves 12. These may include military weapons, clothing, helmets and body armor, as well as sensitive equipment such as computers, test equipment, optical devices, electronic devices, communications equipment, and the like.

The contaminant may comprise one or more chemical, biological, radiological or nuclear (CBRN) warfare agents. These may include biologically active substances such as pathogens, biotoxins, prions, spores, vegetative bacteria, viruses, and chemical agents such as nerve gas or blistering agents including VX, GD and HD, and the like.

The decontaminants may comprise one or more liquid phase sterilants or decontaminants such as peracids (e.g., peracetic acid) and/or peroxides, and/or vapor phase sterilants or decontaminants such as peroxides, for example, hydrogen peroxide, and the like. The vaporous hydrogen peroxide may be used in combination with ammonia. Other oxidants such as hypochlorites, solutions of ozone, and the like, may be used.

The decontamination process that is conducted in the cabinet 102 may comprise a sterilization process or a less rigorous process, for example, a disinfection process, a sanitization process, a cleaning process, and the like. The term "sterilization" may refer to rendering a biological organism totally incapable of reproduction, metabolism and/or growth. The term "sterilization" may refer to the complete destruction of a chemical, radiological or nuclear warfare agent or conversion of the same to a non-harmful substance. The less rigorous processes contemplated herein may render an article free from harmful substances or living organisms to a degree determined to be acceptable.

The shelf assembly 10 as well as the decontamination unit 100 may be constructed using any material that is sufficient to provide the apparatus with the required properties of strength and resistance to anticipated operating conditions and hazards, including hot and cold temperatures, chemical exposure, and the like, that would be required for its intended use. These materials may include one or more of stainless steel, coated steel, aluminum, anodized aluminum, and the like. Various metal alloys may be used, including the stainless steel alloys SS304 and SS316, and aluminum alloy 6061. Non-reactive materials, such as polytheylene, polyvinyl chloride, fluorinated polymers such as polytetrafluoroethylene, and the like, may be used in the construction of the shelf assembly 10 and/or the decontamination unit 100.

The shelf assembly 10 as well as the decontamination unit 100 may be ruggedized to withstand hostile environments such as those that may be encountered in military applications. The term "ruggedized" is used herein to refer to apparatus that is: (1) hardened to ensure that five exposures to chemical, biological, radiological or nuclear (CBRN) contaminants, decontaminants and decontaminating procedures over a thirty-day period do not cause the apparatus to require corrective maintenance during that thirty-day period; (2) capable of being used at temperatures ranging from about $-32°$ C. to about $49°$ C.; (3) capable of being used in relative humidities ranging from about 5% to about 100%; and/or (4) capable of operating when exposed to conventional hazards of solar radiation, rain, fungus, salt fog, sand, dust, vibration and/or shock in accordance with Military Standard 810 (MIL-STD-810).

While the disclosed invention has been explained in relation to various detailed embodiments, it is to be understood that various modifications thereof may become apparent to those skilled in the art upon reading the specification. Therefore, it is to be understood that the invention specified herein is intended to include such modifications as may fall within the scope of the appended claims.

The invention claimed is:
1. A ruggedized decontamination unit, comprising:
a cabinet comprising at least one shelf assembly;
the shelf assembly comprising
   a shelf that is slideable in a first direction and a second direction, the shelf comprising a first end and second end;
   a first stationary support and a second stationary support, the first stationary support being positioned opposite the second stationary support, the first and second stationary supports slidably supporting the shelf, the first stationary support having a first end and a second end, the second stationary support having a first end and a second end;

a first stationary stop mounted on the first stationary support near the first end of the first stationary support;

a first traveling stop positioned near the second end of the shelf and adapted for directly contacting the first stationary stop when the shelf slides in the first direction;

a second stationary stop mounted on the second stationary support near the second end of the second stationary support; and a second traveling stop positioned near the first end of the shelf and adapted for directly contacting the second stationary stop when the shelf slides in the second direction;

the cabinet including a first entrance with a first door and a second entrance with a second door, the first entrance being suitable for permitting one or more shelves to partially extend out of the cabinet through the first entrance when slid in the first direction, the second entrance being suitable for permitting one or more shelves to partially extend out of the cabinet through the second entrance when slid in the second direction; and a decontaminant generator for generating a decontaminant in the cabinet, wherein the decontamination unit includes components (1) to harden said decontamination unit to withstand five exposures to chemical, biological, radiological or nuclear contaminants, decontaminants and decontaminating procedures over a thirty-day period do not cause the apparatus to require corrective maintenance during that thirty-day period; and so that said decontamination unit is (2) capable of being used at temperatures ranging from about −32° C. to about 49° C.; (3) capable of being used in relative humidities ranging from about 5% to about 100%; and (4) capable of operating when exposed to conventional hazards of solar radiation, rain, fungus, salt fog, sand, dust, vibration and shock.

2. The decontamination unit of claim 1 wherein the shelf is rectangular and has a first longitudinal frame member and a second longitudinal frame member, the shelf assembly further comprising a first sliding support attached to the first longitudinal frame member and a second sliding support attached to the second longitudinal frame member, the first traveling stop being mounted on the first sliding support, the second traveling stop being mounted on the second sliding support.

3. The decontamination unit of claim 2 wherein a first sliding shelf rail is attached to the first sliding support and a second sliding shelf rail is attached to the second sliding support, the first stationary support comprising a plurality of first rollers adapted to be received by the first sliding shelf rail, the second stationary support comprising a plurality of second rollers adapted to be received by the second sliding shelf rail.

4. The decontamination unit of claim 3 wherein the first and second sliding shelf rails comprise open channels with upper and lower flanges, the first rollers comprising wheels mounted on the first stationary support and adapted to be received by the open channel of the first sliding shelf rail, the second rollers comprising wheels mounted on the second stationary support and adapted to be received by the open channel of the second sliding shelf rail.

5. The decontamination unit of claim 2 wherein the first traveling stop comprises a projection extending vertically from the first sliding support and the second traveling stop comprises a projection extending vertically from the second sliding support.

6. The decontamination unit of claim 2 wherein the spacing of stationary stops from the ends of the stationary supports and the spacing of the traveling stops from the ends of the sliding supports is sufficient to permit a horizontal sliding movement of the shelf in the first and second directions but not substantial tipping.

7. The decontamination unit of claim 1 wherein the shelf comprises a rectangular frame having a grid of supports running the width and length of the rectangular frame.

8. The decontamination unit of claim 1 wherein the first stationary stop comprises a projection extending horizontally and vertically from the first stationary support and the second stationary stop comprises a projection extending horizontally and vertically from the second stationary support.

9. The decontamination unit of claim 1 wherein the first stationary stop and the first traveling stop are positioned to permit a sliding movement of the shelf in the first direction beyond the first stationary stop to the extent up to about 85% of the length of shelf as measured from the first end of the shelf to the second end of the shelf.

10. The decontamination unit of claim 1 wherein the second stationary stop and the second traveling stop are positioned to permit a sliding movement of the shelf in the second direction beyond the second stationary stop to the extent up to about 85% of the length of shelf as measured from the second end of the shelf to the first end of the shelf.

11. The decontamination unit of claim 1 wherein the first stationary support is mounted on a first interior wall of the cabinet and the second stationary support is mounted on a second interior wall of the cabinet, the first interior wall being opposite the second interior wall.

12. A method of operating the decontamination unit of claim 1, comprising:

opening the first door;

extending one or more of the shelves in the first direction partially through the first entrance;

placing one or more contaminated articles on the one or more partially extended shelves;

sliding the one or more partially extended shelves in the second direction into the cabinet;

closing the first door;

operating the decontaminant generator to generate a decontaminant in the cabinet for a sufficient period of time to decontaminate the one or more contaminated articles to product one or more decontaminated articles;

opening the second door;

extending the one or more shelves in the second direction partially through the second entrance; and removing the one or more decontaminated articles from the one or more partially extended shelves.

* * * * *